(12) United States Patent
Deville et al.

(10) Patent No.: US 9,388,332 B2
(45) Date of Patent: Jul. 12, 2016

(54) CHEMICALLY TAGGED POLYMERS FOR SIMPLIFIED QUANTIFICATION AND RELATED METHODS

(71) Applicant: Halliburton Energy Services, Inc., Houston, TX (US)

(72) Inventors: Jay Paul Deville, Houston, TX (US); Phillip Wayne Livanec, Houston, TX (US); Sherif Eldin, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 322 days.

(21) Appl. No.: 13/663,613

(22) Filed: Oct. 30, 2012

(65) Prior Publication Data

US 2014/0116778 A1 May 1, 2014

(51) Int. Cl.
*C09K 8/03* (2006.01)
*E21B 47/10* (2012.01)
*G01N 1/10* (2006.01)

(52) U.S. Cl.
CPC .............. *C09K 8/03* (2013.01); *E21B 47/1015* (2013.01); *G01N 1/10* (2013.01); *G01N 2001/1031* (2013.01)

(58) Field of Classification Search
CPC .................................................. E21B 47/1015
USPC ............................ 175/42; 165/250.12; 702/9
See application file for complete search history.

(56) References Cited

U.S. PATENT DOCUMENTS

| | | | |
|---|---|---|---|
| 5,849,590 A * | 12/1998 | Anderson, II ......... | C06B 23/008 436/106 |
| 5,905,061 A | 5/1999 | Patel | |
| 5,977,031 A | 11/1999 | Patel | |
| 6,670,605 B1 * | 12/2003 | Storm, Jr. ............... | E21B 49/08 250/255 |
| 6,828,279 B2 | 12/2004 | Patel et al. | |
| 6,925,392 B2 | 8/2005 | McNeil, III et al. | |
| 7,337,660 B2 | 3/2008 | Ibrahim et al. | |
| 7,472,748 B2 | 1/2009 | Gdanski et al. | |
| 7,534,745 B2 | 5/2009 | Taylor et al. | |
| 7,571,644 B2 | 8/2009 | Ibrahim et al. | |

(Continued)

FOREIGN PATENT DOCUMENTS

| | | |
|---|---|---|
| WO | 2005054830 A1 | 6/2005 |
| WO | 2005055236 A1 | 6/2005 |

(Continued)

OTHER PUBLICATIONS

Davison et al., "Rig-Site Monitoring of the Solids Content of Drilling Fluid and Discharges from Solids Control Equipment," SPE 36831, 1996.

(Continued)

*Primary Examiner* — Angela M DiTrani
*Assistant Examiner* — Ryan Schneer
(74) *Attorney, Agent, or Firm* — McDermott Will & Emery LLP; Craig Roddy

(57) ABSTRACT

Method comprising the steps of obtaining a sample of a return drilling fluid, the return drilling fluid containing a tagged detectable additive, the tagged detectable additive comprising a polymer comprising at least one chemical tag bonded to the polymer; and determining a concentration of the tagged detectable additive in the return drilling fluid based on a spectroscopic signal of the sample. The tagged detectable additive may include a polymer comprising at least one chemical tag bonded to the polymer.

17 Claims, 2 Drawing Sheets

(56) References Cited

U.S. PATENT DOCUMENTS

| | | | |
|---|---|---|---|
| 7,645,723 B2 | 1/2010 | Kirsner et al. | |
| 7,696,131 B2 | 4/2010 | Oyler et al. | |
| 2001/0018503 A1* | 8/2001 | Whipple | B01D 21/01 |
| | | | 526/240 |
| 2001/0036667 A1* | 11/2001 | Tayebi | E21B 47/1015 |
| | | | 436/56 |
| 2003/0021998 A1 | 1/2003 | Hubbard et al. | |
| 2004/0098202 A1* | 5/2004 | McNeil, III | G01N 33/2823 |
| | | | 702/12 |
| 2005/0109087 A1* | 5/2005 | Robb | E21B 47/1015 |
| | | | 73/53.01 |
| 2005/0256647 A1* | 11/2005 | Ellis | G01N 33/2823 |
| | | | 702/9 |
| 2006/0052251 A1* | 3/2006 | Anderson | E21B 47/1015 |
| | | | 507/103 |
| 2006/0144588 A1* | 7/2006 | Ferguson | E21B 47/1015 |
| | | | 166/252.6 |
| 2006/0254985 A1* | 11/2006 | Morris | C08F 220/56 |
| | | | 210/724 |
| 2009/0087912 A1* | 4/2009 | Ramos | C09K 8/032 |
| | | | 436/27 |
| 2009/0095534 A1* | 4/2009 | Perez | C09K 8/524 |
| | | | 175/65 |
| 2010/0268074 A1* | 10/2010 | Van Loef | A61B 6/032 |
| | | | 600/431 |
| 2011/0005310 A1 | 1/2011 | Lunkad et al. | |
| 2011/0167896 A1* | 7/2011 | Hershey | E21B 47/1015 |
| | | | 73/38 |

FOREIGN PATENT DOCUMENTS

| | | |
|---|---|---|
| WO | 2009050432 A1 | 4/2009 |
| WO | 2014070638 A1 | 5/2014 |

OTHER PUBLICATIONS

International Search Report and Written Opinion for PCT/US2013/067014 dated Jan. 21, 2014.

Extended European Search Report dated Apr. 13, 2016 for EP 13850422.0.

* cited by examiner

CHEMICALLY TAGGED POLYMERS FOR SIMPLIFIED QUANTIFICATION AND RELATED METHODS

BACKGROUND

The present disclosure relates to methods and compositions for use in drilling operations. Particularly, the present disclosure is directed toward tagged detectable additives for use in drilling fluids and methods of detection and quantification thereof.

Many subterranean operations involve the drilling of a well bore from the surface through rock and/or soil to penetrate a subterranean formation containing fluids that are desirable for production. In the course of drilling operations and other subterranean operations, the drill string and/or other equipment may contact zones of rock and/or soil containing tar (e.g., heavy hydrocarbons, heavy oil, asphalt, bitumens, and the like); in many such operations, it may be desirable to drill the well bore through these tar-containing zones. However, tar is a relatively tacky substance that may readily adhere to surfaces that it contacts, including the surfaces of the well bore and/or any equipment utilized therein.

Tar also may dissolve into many synthetic treatment fluids used in the course of drilling operations, increasing the tacky and adhesive properties of the tar and affecting the rheological profile of the treatment fluid. If a sufficient amount of tar dissolves into the treatment fluid, the tar may contact and adhere to surfaces of equipment used in the well bore or the well bore itself. This may, among other problems, prevent the drill string from rotating, prevent fluid circulation, or otherwise impede the effectiveness of a drilling operation. In some cases, it may become necessary to remove and/or disassemble the drill string in order to remove accretions of tar, a process that may create numerous cost and safety concerns. The accretion of tar on drilling equipment and/or in the well bore also can impede any subsequent operations, including cementing, acidizing, fracturing, sand control, and remedial treatments. In addition, soft, tacky tar that manages to reach the surface may foul surface equipment, including solids screening equipment.

Existing methods of managing these tar incursion problems may be problematic. Some of these methods involve affecting an increase in hydrostatic pressure in the well bore so as to force the tar out of the well bore to the surface. However, this increased hydrostatic pressure may damage the well bore and/or a portion of the subterranean formation.

Other conventional methods utilize treatment fluids that comprise dispersants, surfactants, and/or solubilizers, which allow the tar particles to dissolve in or homogenize with the treatment fluids. However, the tar particles may not be readily separated out of the fluid once they have dissolved into or homogenized with the fluid. The presence of the tar particles in the treatment fluid may alter its rheological properties and/or suspension capacity, which may limit its use in subsequent operations. Moreover, the addition of these dispersants, surfactants, and solubilizers may increase the complexity and cost of the drilling operation.

Polymers, both natural and synthetic, are utilized in the drilling and completion of subterranean wells in a variety of functions, such as components of treatment fluids to overcome the aforementioned tar accretion problem. These treatment fluids may comprise an aqueous fluid and a polymer. As used herein, the term "treatment fluid" refers to any fluid that may be used in a subterranean application in conjunction with a desired function and/or for a desired purpose. The term "treatment fluid" does not imply any particular action by the fluid or any component thereof. A polymeric material may be ionic or nonionic in nature. The polymers may interact with the tar resident in a well bore such that the properties of the tar are altered. Optionally, the polymer may bind or coat the tar such that the tar becomes less sticky. Thus, the polymer(s) should be added to the well bore in a quantity sufficient to treat the tar therein.

However, as the polymers are utilized during drilling operations, the amount of polymers is diminished. When the level of polymer in the treatment fluid gets below a certain concentration, the ability of the polymer to perform its intended task is significantly reduced. As such, the ability of ascertaining the concentration of a polymer in a sample of drilling or completion fluid is highly valuable, but often relies on advanced techniques, such as gas chromatography (GC), mass spectroscopy (MS), pyrolysis GC/MS, and the like, which may be unsuitable for application in the field and may not provide real-time data. Samples usually have to be taken away from a well site in order to be tested by such techniques, and then the data returned to the well. In other conventional drilling, drilling operators simply add more polymers to the drilling fluid without actually knowing the amount of polymers remaining in the drilling fluid. This could cause waste of the polymer leading to higher costs of drilling.

Even if suitable techniques for detecting the polymer could be used at the well site, interference resulting from the large number of additives present in drilling and completion fluids, as well as potential interferences from formation fluids, may make these techniques seemingly unsuitable in the field. These interferences may show absorbance/emission bands that overlap with the absorbance/emission bands of the polymers under study. This is particularly true in the ultraviolet region of the electromagnetic spectrum, which is otherwise a very rich region for concentration determination. Despite these limitations, the ease and reliability of a spectrometric method is still thought to be highly desirable for field quantification of polymer concentration.

SUMMARY OF THE INVENTION

The present disclosure relates to methods and compositions for use in drilling operations. Particularly, the present disclosure is directed toward tagged detectable additives for use in drilling fluids and methods of detection and quantification thereof.

In some embodiments, the present invention provides a method comprising obtaining a sample of a return drilling fluid, the return drilling fluid containing a tagged detectable additive, and determining a concentration of the tagged detectable additive in the return drilling fluid based on a spectroscopic signal of the sample. The tagged detectable additive may include a polymer comprising at least one chemical tag bonded to the polymer.

In other embodiments, the present invention provides a drilling fluid comprising a base fluid, and a tagged detectable additive including a polymer comprising at least one chemical tag bonded to the polymer.

The features and advantages of the present invention will be readily apparent to those skilled in the art upon a reading of the description of the preferred embodiments that follows.

BRIEF DESCRIPTION OF THE FIGURES

The drawing figures depict one or more implementations in accord with the present teachings, by way of example only, not by way of limitation. In the figures, like reference numerals refer to the same or similar elements.

DETAILED DESCRIPTION

Figure 1:
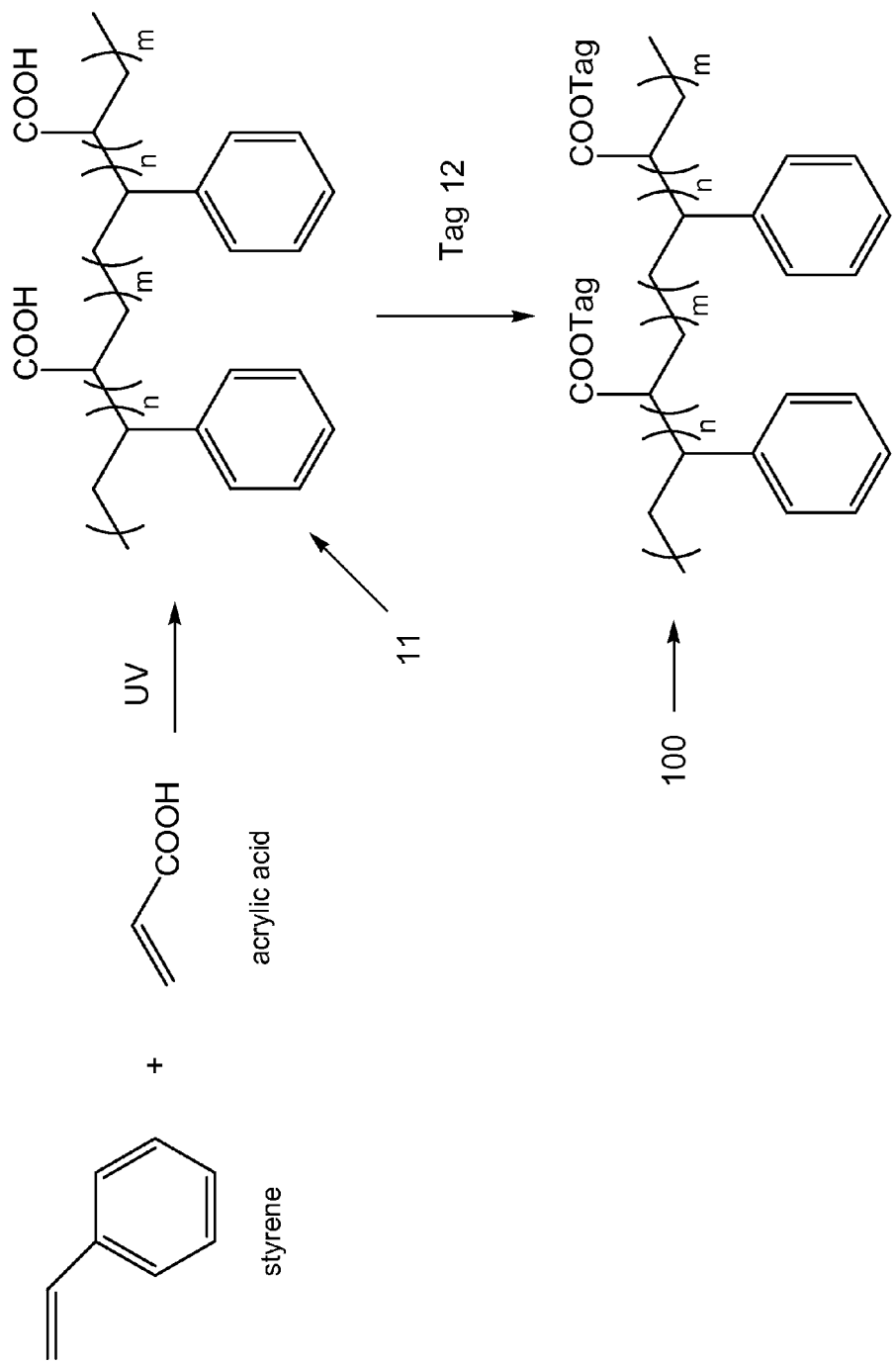
FIG. 1 is a representation of a tagged detectable additive according to one embodiment of the present disclosure.

The present disclosure relates to methods and compositions for use in drilling operations. Particularly, the present disclosure is directed toward tagged detectable additives for use in drilling fluids and methods of detection and quantification thereof.

In order to detect and measure an amount of tagged detectable additive used, for example, as a tar accretion inhibitor in a drilling fluid, an embodiment of the present disclosure may be directed toward a method of obtaining a sample of a return drilling fluid, the return drilling fluid comprising a tagged detectable additive comprising a polymer comprising at least one chemical tag bonded to the polymer. The concentration of the tagged detectable additive in the return drilling fluid may then be determined based on a spectroscopic signal of the sample. As used herein, "return drilling fluid" generally refers to a drilling fluid that has been introduced to a subterranean environment and that has been circulated back up to the surface. In particular, an example of a return drilling fluid may be a drilling fluid that has been used in a drilling operation and that includes various solid contaminants such as drill cuttings, rocks, sand, shale, grit, assorted debris, and other solid contaminants. This method allows a wellbore operator to determine the amount of additive present during drilling operations in a time sufficient to respond if additional additive is needed in the drilling fluid down well to aid in tar accretion inhibition and/or reduction with any of the foregoing aqueous-based fluids or combinations thereof.

A sample of the return drilling fluid may be obtained by any suitable means. In some embodiments, the determination is made on-line in a wellhead. For example, a suitable on-line real-time technique may be a method wherein the detectors are located on a drill head. In this embodiment, the detectors will analyze the drilling fluid while still in the well. For example, the analysis could be UV-Vis spectroscopy. The information obtained from the analysis, for example, the UV-Vis spectrographic data, can then be relayed to an operator at the site or at an offsite location. The operator may then evaluate the concentration of the tagged detectable additive based on the spectrographic data. Then, the operator may then make a decision to add more tagged detectable additive to the well based on the data.

In other embodiments, the detection may be made above ground outside the wellbore. A suitable above ground technique may be spectroscopy wherein fluid samples are collected and analyzed outside the wellbore. An operator will collect samples of the drilling fluid as it exits the well and perform analysis of the sample. The determination can be made immediately, i.e., real-time or any time thereafter, as convenient for the user.

A sample of the return drilling fluid may be obtained by recovering the returned drilling fluid at the well surface, removing drilling cuttings and undesirable drill solids, and obtaining a sample of this drilling fluid before recirculating the reconditioned drilling fluid into the well. The removal or separation of solids from the drilling fluids may be performed using a size exclusion screen. Smaller solids may further be removed, at least partially, by additional processing equipments such as a hydrocyclone or centrifuges. Once the solids are removed, a field operator may sample the return drilling fluid for analysis.

In other examples, the reconditioned drilling fluid may be further subjected to a hydrocyclone or a centrifuge to separate suspensions by density and generate two types of fluids, an overflow and an underflow. The composition of the overflow is the same or very similar to a new drilling fluid and may be reintroduced into the wellbore without further treatment. On the other hand, the underflow is a concentrated fluid comprising much of the unwanted solids present in the returned fluid. One or both of the overflow and/or the underflow may be sampled to determine the concentration of tagged detectable additive.

In some embodiments, a drilling fluid of the present disclosure may comprise a base fluid. Base fluids suitable for use in conjunction with drilling fluids of the present invention may, in some embodiments, include, but are not limited to, oil-based fluids, aqueous-based fluids, aqueous-miscible fluids, water-in-oil emulsions, or oil-in-water emulsions. Suitable oil-based fluids may, in some embodiments, include, but are not limited to, alkanes, olefins, aromatic organic compounds, cyclic alkanes, paraffins, diesel fluids, mineral oils, desulfurized hydrogenated kerosenes, and any combination thereof. Suitable aqueous-based fluids may, in some embodiments, include, but are not limited to, fresh water, saltwater (e.g., water containing one or more salts dissolved therein), brine (e.g., saturated salt water), seawater, acidic aqueous fluids, basic aqueous fluids, and any combination thereof. Suitable aqueous-miscible fluids may, in some embodiments, include, but are not limited to, alcohols (e.g., methanol, ethanol, n-propanol, isopropanol, n-butanol, sec-butanol, isobutanol, and t-butanol), glycerins, glycols (e.g., polyglycols, propylene glycol, and ethylene glycol), polyglycol amines, polyols, any derivative thereof, any in combination with salts (e.g., sodium chloride, calcium chloride, calcium bromide, zinc bromide, potassium carbonate, sodium formate, potassium formate, cesium formate, sodium acetate, potassium acetate, calcium acetate, ammonium acetate, ammonium chloride, ammonium bromide, sodium nitrate, potassium nitrate, ammonium nitrate, ammonium sulfate, calcium nitrate, sodium carbonate, and potassium carbonate), and any combination thereof. In some embodiments, any of the foregoing aqueous-miscible fluids or combinations thereof may be used in combination.

Water-in-oil emulsions or oil-in-water emulsions may also be suitable and may comprise any of the foregoing oil-based fluids, aqueous-based fluids, and aqueous-miscible fluids. Suitable water-in-oil emulsions, also known as invert emulsions, may, in some embodiments, have an oil-to-water ratio ranging from a lower limit of greater than about 50:50, 55:45, 60:40, 65:35, 70:30, 75:25, or 80:20 to an upper limit of less than about 100:0, 95:5, 90:10, 85:15, 80:20, 75:25, 70:30, or 65:35 by volume in the base fluid, where the amount may range from any lower limit to any upper limit and encompass any subset there between. Examples of suitable invert emulsions include, but are not limited to, those disclosed in U.S. Pat. No. 5,905,061 entitled "Invert Emulsion Fluids Suitable for Drilling," U.S. Pat. No. 5,977,031 entitled "Ester Based Invert Emulsion Drilling Fluids and Muds Having Negative Alkalinity," U.S. Pat. No. 6,828,279 entitled "Biodegradable Surfactant for Invert Emulsion Drilling Fluid," U.S. Pat. No. 7,534,745 entitled "Gelled Invert Emulsion Compositions Comprising Polyvalent Metal Salts of an Organophosphonic Acid Ester or an Organophosphinic Acid and Methods of Use and Manufacture," U.S. Pat. No. 7,645,723 entitled "Method of Drilling Using Invert Emulsion Drilling Fluids," and U.S. Pat. No. 7,696,131 entitled "Diesel Oil-Based Invert Emulsion Drilling Fluids and Methods of Drilling Boreholes," the entire disclosures of which are incorporated herein by reference. It should be noted that for water-in-oil and oil-in-water emulsions, any mixture of the above may be used including the water being and/or comprising an aqueous-miscible fluid.

The tagged detectable additives of the present disclosure may include polymer(s) used to treat tar resident in a well bore and associated methods of use that are readily detectable in the drilling fluid because of a chemical tag on the polymer structure.

In some examples, the polymers of the tagged detectable additives may include a styrene-acrylate based copolymers. Examples of suitable styrene-acrylate copolymers may include at least one unit selected from the group consisting of a styrene, a substituted styrene, and any derivative thereof; and at least one unit selected from the group consisting of -acrylate, -methacrylate, -ethylacrylate, -propylacrylate, -butylacrylate, -tert-butyl-acrylate, -n-hydroxyethyl methacrylate, -potassium acrylate, -pentabromobenzyl acrylate, -methyl methacrylate, -ethyl methacrylate, -n-nitrophenyl acrylate, -methyl 2-(acyloxymethyl)acrylate, -cyclohexyl acrylate, -n-ethylhexyl acrylate, and any derivative thereof. However, any polymeric material suitable for use as a tar inhibitor may be used.

The polymer may be any suitable molecular weight for use in drilling operations. In some embodiments, the polymer has a molecular weight of about 10,000 to about 4 million Daltons. In other embodiments, the polymer has a molecular weight of about 100,000 to about 2 million Daltons. In still other embodiments, the polymer has a molecular weight of about 500,000 to about 1 million Daltons.

The tagged detectable additive may include a polymer comprising at least one chemical tag chemically bonded to the polymer. In the example shown in FIG. 1, a tagged detectable additive 100 contains a polymer 11 and chemical tags 12 covalently bonded to the polymer 11. In FIG. 1, the polymer 11 is styrene-acrylate copolymer, formed by the polymerization of styrene and acrylic acid. After the polymerization, the styrene-acrylate copolymer may then be reacted with a chemical tag 12 that reacts with the carboxylic acid group of the acrylate portion of the polymer to be chemically bonded to the polymer to form the tagged detectable additive 100. However, the reaction shown in FIG. 1 is only an example, and other methods and materials for chemically bonding a chemical tag to a polymer may be used.

Figure 2:
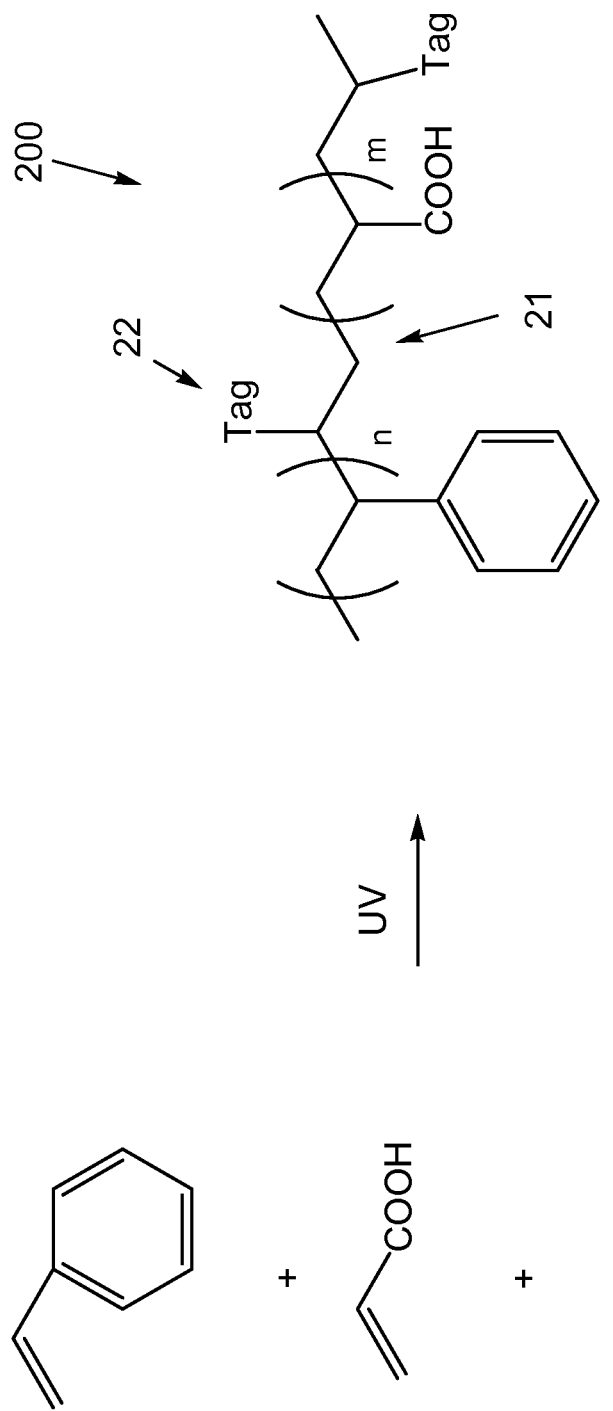
FIG. 2 is a representation of a tagged detectable additive according to another embodiment of the present disclosure.

In other embodiments, the tagged detectable additive may be incorporated into the polymer chain with chemical bonds by polymerization of monomers that comprise the polymer along with the chemical tag. The chemical tag may include a polymerizable portion, for example, a carbon-carbon double bond, so that the chemical tag may react with the monomers and form a polymeric tagged detectable additive. For example, as is shown in FIG. 2, a polymeric additive 200 may be derived from the monomers styrene and acrylic acid, and chemical tags 22 that form one polymeric chain 21 in which the chemical tags 22 are incorporated. As with FIG. 1, the reaction shown in FIG. 2 is only an example, and other methods and materials for chemically bonding a chemical tag to a polymer may be used.

Any suitable method of polymerization may be used to form the tagged detectable additives. In some embodiments, the polymerization of the tagged detectable additive is through emulsion polymerization. Emulsion polymerization is a type of radical polymerization that usually starts with an emulsion incorporating water, monomer, and surfactant. The most common type of emulsion polymerization is an oil-in-water emulsion, in which droplets of monomer (the oil) are emulsified (with surfactants) in a continuous phase of water. One advantage of using emulsion polymerization is the ability to control the molecular weight of the polymer.

In other examples, the detectable compound may be a counter-ion that when introduced into a mixture containing an ionic polymer, the detectable compound may supplant the currently existing counter-ion. The detectable compound can then be held in the polymer via an ionic bond.

The amount of chemical tags incorporated into or chemically bonded to the polymer should be sufficient to enable an operator to detect the presence and determine the concentration of the tagged detectable additive in the drilling fluid, for example, by the UV-Vis spectrophotometer. For example, the amount of chemical tag in the polymer may be from about 0.0001 to about 10 mol %.

The chemical tag may be detected by any means of identification. For example, the chemical compound may be detected via infrared (IR) spectroscopy, Ultraviolet-Visible (UV-Vis) spectroscopy, fluorescence spectroscopy, atomic absorption spectroscopy, atomic emission spectroscopy, and the like.

In order to achieve a spectrum that accurately measures the concentration of the tagged detectable additive and will not suffer interference from other components of the drilling fluid, the chemical tag preferably comprises at least one fluorescent compound. The fluorescent compound may be any suitable compound capable of fluorescence. For example, the fluorescent compound may be one selected from: fluorescein, a fluorescein derivative, fluorescein o-acrylate, fluorescein o-methacrylate, fluorescein dimethacrylate, 3,8-dimethacryloyl ethidium bromide, methacyloxyethyl thiocarbamoyl rhodamine B, and 2'-(4-methacryloxyphenyl)-5-(4-methyl-1-piperazinyl)-2,5'-bibenzimidazolyl trihydrochloride, carboxynaphthofluorescein, boron-dipyrromethene (BODIPY) chromaphores, carboxytetramethylrhodamine and combinations thereof.

In other examples of the present disclosure, the tagged detectable additive may also be identified by isotopic labeling. Isotopic labeling is a technique used to track the passage of an isotope, or an atom with a variation, through a reaction, metabolic pathway, or cell. The reactant is 'labeled' by replacing specific atoms by their isotope. The isotope may be radioactive or stable. Examples of radioactive isotopes include tritium ($^3$H), carbon-14 ($^{14}$C), and nitrogen-13 ($^{13}$N), and oxygen-15 ($^{15}$O).

In isotopic labeling, there are multiple ways to detect the presence of labeling isotopes; through their mass, vibrational mode, or radioactive decay. Mass spectrometry or nuclear magnetic resonance detects the difference in an isotope's mass, while infrared spectroscopy detects the difference in the isotope's vibrational modes. Accelerator mass spectrometry has also been used to detect low levels of radioactivity in samples but is infrequently used due to the expense of the equipment and the difficulty in sample preparation.

The radioactive decay can be detected through an ionization chamber or autoradiographs of gels. Detection of radioactive isotopes may also be performed with liquid scintillation counting (LSC). LSC uses a photomultiplier tube to detect light emissions from the fluor; a fluor is a fluorescent molecule that undergoes excitation by the absorption of radiation and releases light when it relaxes to the ground state. The amount of light emitted by a specified amount of radioactive material can be directly correlated to the amount of radioactivity present. Scintillation-based methods are good for the detection of radiolabels both due to the sensitivity, and due to the difficulties in handling contamination from sample spillage inside an instrument such as an NMR spectrometer.

In order to utilize isotopic labeling, the detectable polymer may incorporate a chemical isotope into the polymer structure as the chemical tag. In some examples, the chemical tag may include a compound containing at least one of $^2$D, $^3$T, $^{13}$C, $^{15}$N, $^{18}$O, $^{31}$P and $^{37}$Cl. In other examples, the chemical tag may include radio-labeled isotopes of at least one from the group consisting of H, C, N, O, F, Br and I. For example, radio-labeled isotopes include $^3$T, $^{11}$C, $^{13}$N, $^{15}$O, $^{18}$F, $^{76}$Br, $^{123}$I and $^{124}$I.

The concentration of the tagged detectable additive with the radio-isotope may be determined in a similar manner as that containing fluorescent compound. The method includes obtaining a calibration curve by measuring the radio-isotope or radio-isotopes for at least two different concentrations of the tagged detectable additive in the drilling fluid. Then, the concentration of the sample is determined by comparing the amount of radio-isotope in the sample to the calibration curve.

The concentration of the tagged detectable additive in the drilling fluid should be such that the detectable compound can be detected by a detection method, for example, one of the methods mentioned above.

The sooner the determination is made after obtaining the sample of the drilling fluid, the sooner an operator may react to the data obtained from the measurements. For example, a wellbore operator may determine, based on the concentration of the tagged detectable additive in the return drilling fluid, that more tagged detectable additive is required in the well. By making this determination more quickly after obtaining the sample of return drilling fluid, the wellbore operator may have more time to supply a sufficient amount of tagged detectable additive to the well. This will allow for less tar accretion during and after drilling.

The concentration of the tagged detectable additive used may vary depending on the type of drilling fluid used. For example, in order to sufficiently inhibit and reduce tar accretion in an oil-based drilling fluid, a concentration of the tagged detectable additive in the oil-based drilling fluid may in the range of 0.25 lb/bbl to 12 lb/bbl. On the other hand, in order to sufficiently inhibit and reduce tar accretion in a water-based drilling fluid, a concentration of tagged detectable additive in a water-based drilling fluid may in the range of 1 lb/bbl to 30 lb/bbl.

In some examples used in the present disclosure for determining a concentration of a tagged detectable additive in a sample of a return drilling fluid, the spectroscopic signal of the sample used to determine the concentration of the tagged detectable additive is UV-Vis spectroscopy. As discussed above, the concentration is determined either in the well, on the drill site near the well, or in an offsite location.

In some embodiments to determine the concentration of the tagged detectable additive, a UV-Vis calibration curve of the return drilling fluid may be obtained by measuring a UV-Vis spectrum of at least two different concentrations of tagged detectable additives in the drilling fluid. In other embodiments, to improve the accuracy of the calibration curve, more than two concentrations of tagged detectable additives may be used.

The at least two different concentrations of tagged detectable additives must be known before measuring, so that a relationship between the concentration of the tagged detectable additive and the UV-Vis spectrum can be obtained. To build a calibration curve the absorption spectra for different concentrations of a solution of the same tagged detectable additives are recorded; the intensity of absorption bands (the absorbance) at the point of maximum absorption, or $\lambda_{max}$, of at least one of the absorption bands is determined and then is plotted the absorbance (maximum of absorption) versus concentration $A=f(c)$. Once the calibration curve is obtained, the concentration of tagged detectable additive in the sample may then be determined by comparing the sample to the calibration curve.

The calibration curve may be made offsite or onsite. As long as the calibration curve can be used to accurately determine the concentration of tagged detectable additive in the return drilling fluid, the location at which the calibration curve is created is optional. However, in some examples, it may be useful to obtain a calibration curve onsite to allow a wellbore operator to obtain a calibration curve of the same batch of tagged detectable additive used down well.

To obtain UV-Vis spectra, a UV-Vis spectrophotometer may be used. A UV-Vis spectrophotometer measures the amount of light absorbed at each wavelength of the UV and visible regions of the electromagnetic spectrum. In a conventional UV-Vis spectrophotometer, a beam of light is split; one half of the beam (the sample beam) is directed through a cell containing the sample. The cell must be transparent to UV and visible light in order to prevent absorption of the beam by the cell. The other half of the beam (the reference beam) is directed through an identical cell that does not contain the compound but only the solvent.

In other examples, back-scatter methods of detection may be used to detect the tagged detectable additive. Back-scatter methods allow for quantification of components when fluids are opaque and therefore prevent the transmission of light in the UV-Vis range. Front-surface fluorescence and backscattering probes are readily available and allow easy quantification of fluorescence in the field. As above, the concentration is determined either in the well, on the drill site near the well, or in an offsite location.

A fiber optic probe coupled to the spectrophotometer and a light source could be used to detect the chemical tag in the detectable polymer. One example of a backscattering probe is the R400-7 Fiber Optic Reflection Probe (commercially available from Oceanoptics, Dunedin, Fla.).

In certain examples of the present disclosure, the UV-Vis spectrum of the chemical tag exhibits a $\lambda_{max}$ in the range of 400 to 750 nm. In other examples, a UV-Vis spectrum of the chemical tag exhibits a $\lambda_{max}$ in the range of 600 to 750 nm. These ranges are chosen to avoid measuring absorbance spectra near the UV range, which may have a great deal of interference from other components of the drilling fluid.

To reduce the amount of tar accretion during drilling operations, an operator may allow the tagged detectable additive to interact with the tar to at least partially reduce the tendency of the tar to adhere to a surface.

The tagged detectable additive may be caused to contact the tar resident in a well bore via a treatment fluid comprising an aqueous fluid and a detectable polymer into a well bore and allowing the tagged detectable additive to interact with tar resident in the well bore to at least partially reduce the tendency of the tar to adhere to a surface. One of ordinary skill in the art, with the benefit of this disclosure, will be able to determine the appropriate amount of time to allow the tagged detectable additive to interact with the tar so as to at least partially reduce the adhesiveness of the tar. In certain embodiments, after the tagged detectable additive has been allowed to interact with the tar, the tar then may be removed from the well bore by any means practicable for the given application.

In addition, the tagged detectable additive may be used with other down well operations. For example, other polymers or non-polymers that could be tagged with a detectable additive could be made and their concentrations monitored by the techniques discussed herein. The present invention is not limited to tar treatment fluids.

The drilling fluids of the present invention optionally may comprise additional components to enhance the performance of the fluid. The drilling fluids of the present invention may comprise any such additional components that do not undesirably interact with the other components of the fluid. Generally, additional components should not emulsify or dissolve the tar sought to be treated. The drilling fluids used in methods of the present invention optionally may comprise any number of additional components, including, but not limited to, salts, surfactants, additional fluid-loss-control additives, gas, nitrogen, carbon dioxide, surface-modifying agents, tackifying agents, foamers, friction reducers, additional corrosion inhibitors, scale inhibitors, catalysts, clay-control agents, biocides, antifoam agents, bridging agents, dispersants, flocculants, $H_2S$ scavengers, $CO_2$ scavengers, oxygen scavengers, lubricants, viscosifiers, breakers, weighting agents (e.g., barite), relative-permeability modifiers, resins, particulate materials (e.g., proppant particulates), wetting agents, coating-enhancement agents, and the like. Weighting agents may be used, for example, in a drilling fluid to provide a density sufficient to, for example, control formation pressures. In certain embodiments, the drilling fluid may have a density in the range of from about 7.5 pounds per gallon ("lb/gal") to about 18 lb/gal, and alternatively from about 12 lb/gal to about 18 lb/gal. One of ordinary skill in the art, with the benefit of this disclosure, will be able to determine which additional components are appropriate for a particular application.

The exemplary fluids disclosed herein may directly or indirectly affect one or more components or pieces of equipment associated with the preparation, delivery, recapture, recycling, reuse, and/or disposal of the disclosed fluids. For example, the disclosed fluids may directly or indirectly affect one or more mixers, related mixing equipment, mud pits, storage facilities or units, fluid separators, heat exchangers, sensors, gauges, pumps, compressors, and the like used generate, store, monitor, regulate, and/or recondition the exemplary fluids. The disclosed fluids may also directly or indirectly affect any transport or delivery equipment used to convey the fluids to a well site or downhole such as, for example, any transport vessels, conduits, pipelines, trucks, tubulars, and/or pipes used to fluidically move the fluids from one location to another, any pumps, compressors, or motors (e.g., topside or downhole) used to drive the fluids into motion, any valves or related joints used to regulate the pressure or flow rate of the fluids, and any sensors (i.e., pressure and temperature), gauges, and/or combinations thereof, and the like. The disclosed fluids may also directly or indirectly affect the various downhole equipment and tools that may come into contact with the chemicals/fluids such as, but not limited to, drill string, coiled tubing, drill pipe, drill collars, mud motors, downhole motors and/or pumps, floats, MWD/LWD tools and related telemetry equipment, drill bits (including roller cone, PDC, natural diamond, hole openers, reamers, and coring bits), sensors or distributed sensors, downhole heat exchangers, valves and corresponding actuation devices, tool seals, packers and other wellbore isolation devices or components, and the like.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:

1. A method comprising:
    obtaining a sample of a return drilling fluid, the return drilling fluid containing a tagged detectable additive, the tagged detectable additive comprising a polymer comprising at least one chemical tag covalently bonded to the polymer wherein the chemical tag comprises a plurality of compounds containing radio-labeled isotopes of at least one from the group consisting of $^{13}N$, $^{18}F$, $^{76}Br$, $^{123}I$, and $^{124}I$; and
    determining a concentration of the tagged detectable additive in the return drilling fluid by measuring the concentration of the at least one radio-labeled isotope in the sample.

2. The method of claim 1, wherein the drilling fluid is an oil-based drilling fluid.

3. The method of claim 2, wherein the concentration of the tagged detectable additive in the oil-based drilling fluid is in the range of 0.25 lb/bbl to 12 lb/bbl.

4. The method of claim 1, wherein the drilling fluid is a water-based drilling fluid.

5. The method of claim 4, wherein the concentration of the tagged detectable additive in the water-based drilling fluid is in the range of 1 lb/bbl to 30 lb/bbl.

6. The method of claim 1, wherein the polymer is a styrene-acrylate based polymer.

7. The method of claim 1, wherein the polymer has a molecular weight of about 10,000 to about 4 million Daltons.

8. The method of claim 1, wherein the polymer has a molecular weight of about 100,000 to about 2 million Daltons.

9. The method of claim 1, wherein the polymer has a molecular weight of about 500,000 to about 1 million Daltons.

10. The method of claim 1, further comprising the steps of:
before use of the drilling fluid for the drilling operation, adding a known amount of the radio-labeled isotope to the drilling fluid; and
creating a calibration curve by measuring a mass spectrum for at least two different concentrations of the radio-labeled isotope in the drilling fluid,
wherein the concentration of the sample is determined by comparing the spectrum of the sample to the calibration curve.

11. The method of claim 1, further comprising the steps of:
before use of the drilling fluid for the drilling operation, adding a known amount of the radio-labeled isotopes to the drilling fluid;
obtaining a calibration curve by measuring the at least one radio-labeled isotope for at least two different concentrations of the tagged detectable additive in the drilling fluid,
wherein the concentration of the sample is determined by comparing the amount of radio-labeled isotope in the sample to the calibration curve.

12. The method of claim 11, wherein the tagged detectable additive further comprises a styrene-acrylate copolymer.

13. The method of claim 11, wherein the drilling fluid is placed in the well bore to react with tar present at a specific location therein.

14. The method of claim 11, wherein the drilling fluid is placed into the well bore during drilling of the well bore.

15. The method of claim 14, wherein the styrene-acrylate copolymer comprises: at least one unit selected from the group consisting of a styrene, a substituted styrene, and any derivative thereof; and at least one unit selected from the group consisting of -acrylate, -methacrylate, -ethylacrylate, -propylacrylate, -butylacrylate, -tert-butyl-acrylate, -n-hydroxyethyl methacrylate, -potassium acrylate, -pentabromobenzyl acrylate, -methyl methacrylate, -ethyl methacrylate, -n-nitrophenyl acrylate, -methyl 2-(acyloxymethyl) acrylate, -cyclohexyl acrylate, -n-ethylhexyl acrylate, and any derivative thereof.

16. The method of claim 1, further comprising the steps of:
contacting tar resident in a well bore with the tagged detectable additive; and
allowing the tagged detectable additive to interact with the tar to at least partially reduce the tendency of the tar to adhere to a surface.

17. The method of claim 16, wherein the styrene-acrylate copolymer is introduced into the drilling fluid after the drilling fluid contacts the tar in the well bore.

* * * * *